(12) United States Patent
Goncz et al.

(10) Patent No.: US 6,916,611 B2
(45) Date of Patent: Jul. 12, 2005

(54) EXPRESSION VECTOR SYSTEM AND A METHOD FOR OPTIMIZATION AND CONFIRMATION OF DNA DELIVERY AND QUANTIFICATION OF TARGETING FREQUENCY

(75) Inventors: Kaarin Kerr Goncz, St. Albans, VT (US); Dieter Cotter Gruenert, Shelburne, VT (US); Alessia Colosimo, Rome (IT)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/794,689

(22) Filed: Feb. 26, 2001

(65) Prior Publication Data

US 2002/0160514 A1 Oct. 31, 2002

(51) Int. Cl.[7] .............................. C12Q 1/68; C12Q 1/02; C12N 15/87
(52) U.S. Cl. ............................... 435/6; 435/29; 435/465
(58) Field of Search ............................... 435/6, 29, 465

(56) References Cited

U.S. PATENT DOCUMENTS 6,010,908 A * 1/2000 Gruenert et al. ............ 435/463

OTHER PUBLICATIONS

F.M. Ausubel et al., "Current Protocols in Molecular Biology," vol. 1, 2001, pp. 9.6.5–9.6.12 and 9.5.6–9.5.9.
E. Schenborn et al., "Reporter Gene Vectors and Assays," Molecular Biotechnology, 1999, 12:29–44.
K.K. Goncz et al., "Site–Directed Alteration of Genomic DNA by Small–Fragment Homologous Replacement," Methods in Molecular Biology, 2000, 133:85–99.
G. Ko et al., "Gene Targeting on Expression Vector Systems Mediated by SFHR Technique," American Society of Gene Therapy, 1999, p. 119a, Abstract No. 468.
A. Colosimo et al., "Transfer and Expression of Foreign Genes in Mammalian Cells," Biotechniques, 2000, 29(2):314–331.
K.R. Thomas et al., "Targeted disruption of the murine *int–1* proto–oncogene resulting in severe abnormalities in mid-brain and cerebellar development," Nature, 1990, 346:847–850.
E.G. Shesley et al., "Correction of a human $\beta^s$–globin gene by gene targeting," Proc. Natl. Acad. Sci. USA, 1991, 88:4294–4298.
B.H. Koller et al., "Germ–line transmission of a planned alteration made in a hypoxanthine phosphoribosyltransferase gene by homologous recombination in embryonic stem cells," Proc. Natl. Acad. Sci. USA, 1989, 86:8927–8931.
M.R. Capecchi, "Altering the Genome by Homologous Recombination," Science, 1989, 244:1288–1292.
C. Morrison et al., "Extrachromosomal recombination occurs efficiently in cells defective in various DNA repair systems," Nucleic Acids Research, 1996, 24(11):2053–2058.
S. Thompson et al., "Germ Line Transmission and Expression of a Corrected HPRT Gene Produced by Gene Targeting in Embryonic Stem Cells," Cell, 1989, 56:313–321.
G.M. Adair et al., "Targeted homologous recombination at the endogenous adenine phosphoribosyltransferase locus in Chinese hamster cells," Proc. Natl. Acad. Sci. USA, 1989, 86:4574–4578.
S.C. West, "Enzymes and Molecular Mechanisms of Genetic Recombination," Annu. Rev. Biochem., 1992, 61:603–640.
P.C. Orban et al., "Tissue– and site–specific DNA recombination in transgenic mice," Proc. Natl. Acad. Sci. USA, 1992, 89:6861–6865.
K.K. Goncz et al., "Targeted replacement of normal and mutant CFTR sequences in human airway epithelial cells using DNA fragments," Human Molecular Genetics, 1998, 7(12):1913–1919.
S.L. Mansour et al., "Disruption of the proto–oncogene *int–2* in mouse embryo–derived stem cells: a general strategy for targeting mutations to non–selectable genes," Nature, 1988, 336:348–352.

* cited by examiner

*Primary Examiner*—David Guzo
*Assistant Examiner*—Daniel M. Sullivan
(74) *Attorney, Agent, or Firm*—Gates & Cooper LLP

(57) ABSTRACT

An expression vector system comprising a pair of expression vectors constructed from a wild-type and a mutant version of a maker, reporter or selection gene, and a method for optimization and confirmation of DNA delivery and of gene targeting and for quantification of targeting frequency. Novel prokaryotic/eukaryotic DNA vectors used for DNA delivery and gene targeting assessment and targeting frequency quantification.

19 Claims, 7 Drawing Sheets pZamp+4 pZamp+4
(corrected)

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gcgcgcgacg tcgccggagc g                                            21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
aacaagtttc gaggtcgacc cc                                           22

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
taggagggcc accatggcca                                              20

<210> SEQ ID NO 4
<211> LENGTH: 17
<212> TYPE: DNA
<213> ORGANISM: Artificial Sequence
<220> FEATURE:
<223> OTHER INFORMATION: fragment of Zeocin antibiotic resistance gene

<400> SEQUENCE: 4
ttctcccggg acttctt                                                 17

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
tacgactcac tataggaggg cc                                           22

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ctactcaaac ctgtttggtg ttg                                          23

<210> SEQ ID NO 7
<211> LENGTH: 23

```
<212> TYPE: DNA
<213> ORGANISM: Artificial Sequence
<220> FEATURE:
<223> OTHER INFORMATION: Primer

<400> SEQUENCE: 7
cataacttac ggtaaatggc ccg                                          23

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
cgttccaatg caccgttccc g                                            21

<210> SEQ ID NO 9
<211> LENGTH: 21
<212> TYPE: DNA
<213> ORGANISM: Artificial Sequence
<220> FEATURE:
<223> OTHER INFORMATION: fragment of Zeocin antibiotic resistance gene

<400> SEQUENCE: 9
ttctcccggc cgggacttct t                                            21

<210> SEQ ID NO 10
<211> LENGTH: 43
<212> TYPE: DNA
<213> ORGANISM: Artificial Sequence
<220> FEATURE:
<223> OTHER INFORMATION: fragment of Zeocin antibiotic resistance gene

<400> SEQUENCE: 10
gaccggctcg ggttctcccg gccgggactt cgtggaggac gac                    43

<210> SEQ ID NO 11
<211> LENGTH: 43
<212> TYPE: DNA
<213> ORGANISM: Artificial Sequence
<220> FEATURE:
<223> OTHER INFORMATION: fragment of Zeocin antibiotic resistance gene

<400> SEQUENCE: 11
gaccggctcg ggttctcccg ggacttcgtg gaggacgact tcg                    43

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
acgaagtccc ggccgggaga a                                            21
```

EXPRESSION VECTOR SYSTEM AND A METHOD FOR OPTIMIZATION AND CONFIRMATION OF DNA DELIVERY AND QUANTIFICATION OF TARGETING FREQUENCY

This invention was supported by NIH grants NHDK 46002, DK47766, and grants from the Cystic Fibrosis Foundation and from Cystic Fibrosis Research, Inc. The government may have rights to this invention.

BACKGROUND OF THE INVENTION

1. Field of the Invention

This invention concerns an expression vector system comprising a pair of expression vectors constructed from a wild-type and a mutant version of any marker gene, including a reporter or selection gene, and a method for optimization and confirmation of DNA delivery and of gene targeting and for quantification of targeting frequency. In particular, the invention concerns and embodies pairs of novel prokaryotic/eukaryotic DNA expression vectors used for DNA delivery and gene targeting assessment and targeting frequency quantification. The vector pairs permit assessment and confirmation of DNA delivery as well as optimization of the DNA delivery efficiency and gene targeting in eukaryotic systems and quantification of targeting frequency. The invention further permits assessment of nuclear delivery of the DNA, assessment of cell enzymatic function and assessment of cell enzymatic pathways.

2. Background and Related Disclosures

Gene targeting, as a strategy for gene therapy, provides a mechanism for achieving permanent, site-specific correction of DNA lesions and results in the cell-appropriate expression of the target gene (*Gene Ther.*, 5:149 (1998) and *Gene Ther.*, 6:1347 (1999)).

A gene targeting strategy allows the integrity and regulation of the gene to be maintained even when cis-acting regulatory elements are distant from the coding sequences as described in *Trends in Genetics*, 15:403 (1999) or are within introns as described in *J. Biol. Chem.*, 271:9947 (1996). In addition, the non-viral gene delivery strategies used to introduce the targeting DNA into cells, mitigate the immune and inflammatory side-effects triggered by viral capsid antigens and unmethylated CpG sequences present in cDNA expression plasmids as described in *PNAS (USA)*, 91:4407 (1994), *PNAS (USA)*, 83:2879 (1996) and *Gene Ther.*, 6:1448 (1999).

Small fragment homologous replacement (SFHR) is a gene targeting strategy that has been successfully used to target and modify genomic DNA sequences through the introduction of small fragments of DNA homologous to specific genomic loci in human epithelial cells. SFHR was disclosed in the U.S. Pat. No. 6,010,908, issued on Jan. 4, 2000, hereby incorporated by reference. SFHR was initially used to correct the ΔF508 mutation, the most common lesion associated with the cystic fibrosis transmembrane conductance regulator (CFTR) gene, in CF airway epithelial cells. The DNA fragments were comprised of a 491-bp wild-type (wt) CFTR sequence that would replace the three deleted nucleotides that characterize the ΔF508 mutation. As a result, wtCFTR mRNA expression and the functional correction of the cAMP-dependent Cl-transport defect associated with CF was observed and is further described in *Gene Ther.*, 3:859 (1996). A targeting frequency of 1–10% was indicated in this study.

In a parallel study, targeting DNA fragments comprising genomic ΔF508 CFTR sequence (488-bp) were able to delete the three nucleotides that constitute the ΔF508 mutation gene in the genomic DNA of normal human airway epithelial cells as described in *Hum. Mol. Genet.*, 7:1913 (1998).

For the successful application of SFHR as a gene therapy, optimization of the conditions for targeting is necessary. A drawback of having CFTR as the target gene is the lack of an endogenous selection mechanism that readily differentiates between targeted and parental cells and, thus, limits the ability to accurately quantify targeting frequency.

Additionally, there are currently no established biological assays available for rapid determination of the amount of transfected DNA that was successfully delivered into the cell nucleus and there are no commercial products, methods or assays for determination of site-specific modification of genomic sequences.

While the SFHR method provides a convenient and effective way to alter DNA sequences, determination of the replacement efficiency is still problematic. Inaccessible gene targeting elements and/or target vector and/or a cell system that does not support gene targeting can decrease the gene targeting efficiency. Low gene targeting frequencies can be caused by a DNA delivery system that interferes with the enzymatic pathway(s)/machinery that mediates modification of the target sequences.

It would, therefore, be advantageous to have available a system and/or method and/or means to permit a confirmation of the nuclear DNA delivery efficacy, the optimization of such delivery and quantification of targeting frequency.

It is, therefore, a primary objective of the current invention to provide a means and method for optimization of the DNA delivery efficiency, confirmation of the DNA delivery and quantification of targeting frequency of SFHR-mediated modification of target DNA.

All patents, patent applications and publications described herein are being incorporated by reference.

SUMMARY

One aspect of the current invention is a method for evaluation, optimization of DNA nuclear delivery and gene targeting and for quantification of targeting frequency.

Another aspect of the current invention concerns an expression vector system comprising a pair of expression vectors constructed from a wild-type and a mutant version of a reporter or selection gene for optimization of DNA delivery efficacy, for gene targeting, for confirmation of the DNA delivery and for quantification of targeting frequency.

Still another aspect of the current invention concerns a pair of prokaryotic or eukaryotic DNA vectors suitable for DNA delivery wherein one vector is constructed from a wild-type and a second vector is constructed from a mutant version of a reporter or selection gene.

Still another aspect of the current invention concerns a combination of a wild-type selectable or reporter gene with a mutant version of said selectable or reporter gene.

Still yet another aspect of the current invention is a vector pair utilizing a wild type and mutant version of Zeocin™ antibiotic resistance gene (zeo$^r$).

Still another aspect of the current invention concerns pZamp vector containing a wild-type, functional copy of the zeo$^r$ gene and the second vector, pZamp+4 containing a mutant, nonfunctional copy of the gene.

Yet another aspect of the current invention is the vector pZamp developed by the introduction of the ampicillin resistance (amp$^r$) gene (fragment SalI-PvuII) from pcDNA3 into the multiple cloning site (XhoI-PvuII) of pZeoSV where the pZeoSV vector contains the zeo$^r$ gene under CMV eukaryotic and EM-7 prokaryotic promoters.

Yet another aspect of the invention is the vector pZamp+4 developed by linearizing the pZamp vector at a unique XmaI restriction cleavage site within the zeo$^r$ gene coding sequence, wherein the linearized vector is incubated with Klenow enzyme to fill in the overlapping bases and then ligated and wherein the pZamp+4 vector carries a 4-bp insertion that eliminates the XmaI restriction site and is not resistant to the zeocin antibiotic in either prokaryotic or eukaryotic cells.

Still yet another aspect of the current invention is a method for determination of the efficiency of DNA delivery and its optimization said method comprising use of a pair of expression vectors comprising wild-type and a mutant version of a selectable or reporter gene in any DNA delivery system.

Still yet another aspect of the current invention is a method for quantification of targeting frequency said method comprising use of a pair of expression vectors comprising wild-type and a mutant version of a selectable or reporter gene in any DNA delivery system.

Still another aspect of the current invention is a method for determination of gene targeting efficiency and frequency using a pair of pZamp and pZamp+4 vectors.

BRIEF DESCRIPTION OF DRAWINGS

FIG. 3 depicts a molecular analysis following transient transfection with Zamp+4 and Zeo1 fragments.

DEFINITIONS

Figure 1:
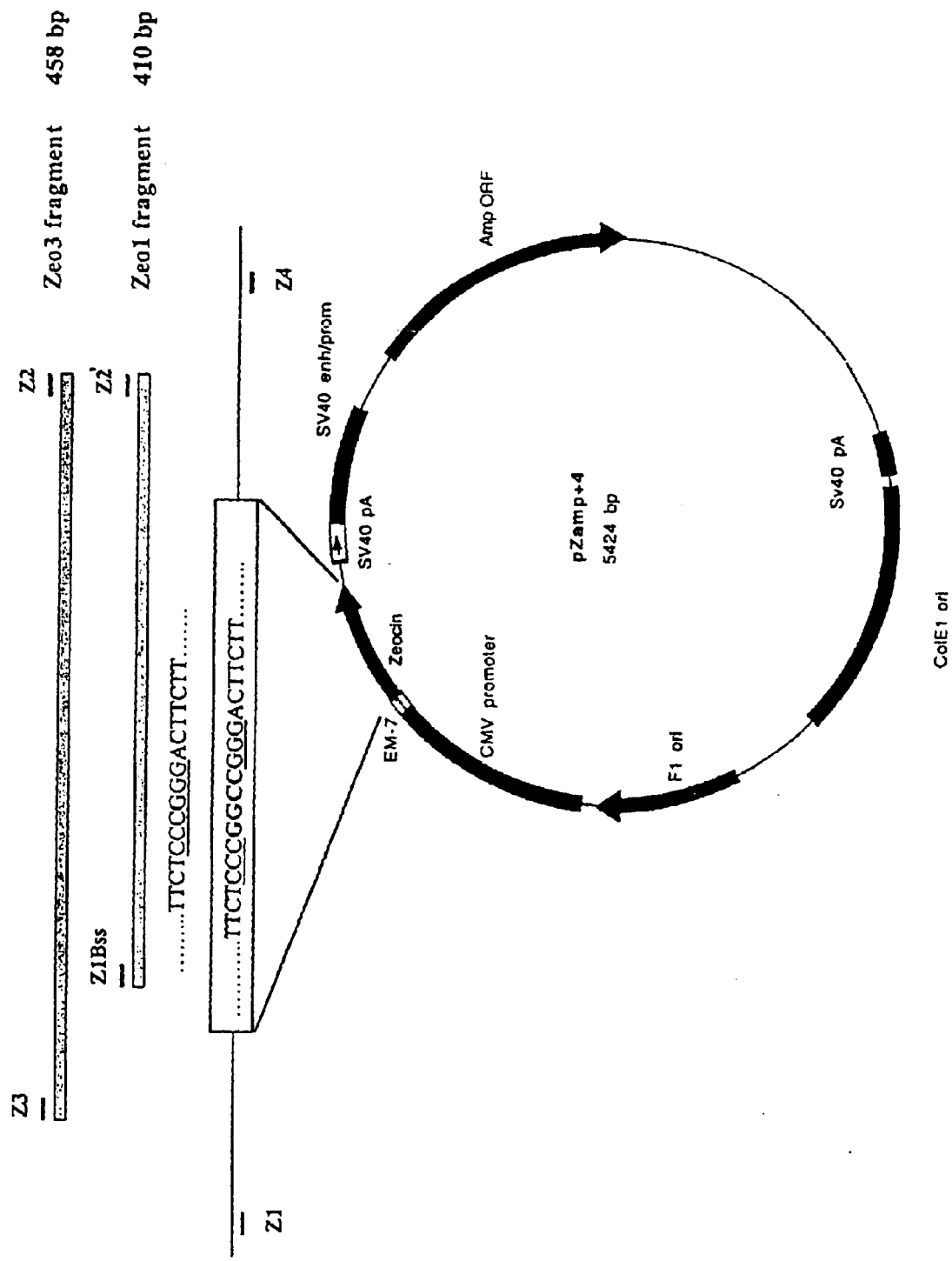
FIG. 1 is a schematic representation of the exemplary defective plasmid (pZamp+4), replacement fragments and primer locations (SEQ ID NOS: 4 and 9, respectively).

"SFHR" means small fragment homologous replacement.

"Prokaryotic" means a cellular organism characterized by the prokaryotic condition, size of about 0.2–10μ, and absence of the nuclear organization paired organized chromosomes, mitotic capacities and complex organelles observed and present in eukaryotes.

"Eukaryotic" means a cell containing a membrane-bound nucleus with chromosomes, DNA, RNA and proteins, typically of sizes 10–100μ, able to undergo cell division, mitosis and containing typical cellular organelles such as mitochondria, plastids, cilia, flagella, etc.

"DOTAP" means the cationic lipid dioleoyltrimethylammonium-propane (DOTAP) used as a delivery vehicle for DNA into cells.

"Marker gene" means any gene which is not expressed in the cell and which is detectable by enzymatic, calorimetric, fluorescence, cell survival, isotopic, chemiluminescent, bioluminescent, ELISA or in situ visualization assays. Examples of the marker genes are reporter or selection genes and any other gene falling within the marker gene definition.

"Reporter gene" means a gene that is not endogenously expressed in the used cell type which is typically used to evaluate another gene, especially its regulatory region. Reporter gene's phenotopic expression is easy to monitor. Representative reporter genes are chloramphenicol acetyl transferase gene (CAT), β-galactosidase gene (β-gal), luciferase gene (luc), alkaline phosphatase gene (AP), secreted alkaline phosphatase gene (SEAP), β-glucuronidase gene (GUS), green fluorescent protein gene (GFP), human growth hormone gene (hGH) and β-lactamase gene (β-lac).

"Selection gene" or "selectable gene" means a gene encoding a protein product which protects cells from substances that would normally be toxic to the cell, such as, for example, antibiotics. Representative selectable genes are aminoglycoside phosphotransferase II gene (neo G418, APH), hygromycin-B-phosphotransferase gene (hygr), bleomycin resistance gene (bleo), zeocin gene (zeo), sulfonamide resistance gene (sull), hypoxantine phosphoribosyl transferase gene (HPRT), adenine phosphoribosyl transferase gene (APRT), adenosine deaminase gene (ADA), cytosine deaminase gene (CDA), dihydrofolate reductase gene (DHFR), histidinol dehydrogenase gene (hisD), puromycin-N-acetyl transferase gene (PAC), thymidine kinase gene (TK), xanthine-guanine phosphoribosyltransferase gene (gpt), diphtheria toxin gene (DT) and herpes simplex virus thymidine kinase gene (HSV-TK).

DETAILED DESCRIPTION OF THE INVENTION

The invention described herein concerns a means and methods suitable for assessment of DNA nuclear delivery. The assessment comprises optimization of DNA delivery, confirmation of DNA delivery and gene targeting, determination of efficacy of DNA delivery and quantification of targeting frequency. The methods and vectors described herein permit assessment of nuclear delivery of the DNA, confirmation of successful DNA delivery, determination of the efficacy of such DNA delivery as well as optimization of such efficacy for DNA nuclear delivery, and, for the first time, permit also quantification of targeting frequency.

The means for achieving these aims is a pair of vectors comprising a combination of prokaryotic/eukaryotic DNA expression vectors constructed from a wild type and a mutant version of a reporter or selection gene.

The invention is particularly useful for confirmation of a novel gene targeting strategy, namely small fragment homologous replacement (SFHR), used to correct specific genomic lesions in human epithelial cells of which the frequency of targeting was estimated to be 1–10% yet the precision of the measurement was limited by the systems used. However, given the genomic target, such as the cystic fibrosis transmembrane conductance regulator (CFTR) gene, until now it was difficult to accurately quantify targeting frequency.

A vector pair comprising a wild-type and mutant marker, selectable or reporter gene described herein permits more accurate and rapid quantification of gene targeting efficiency.

The method of the invention is suitable for assessment of DNA nuclear delivery and determination of the percent number of expression vectors that are transferred into the nucleus by counting the number of bacterial colonies after bacterial transformation of the expression vector isolated from the nucleus of the cell compared to the number of bacterial colonies that result from the vector isolated from whole cells.

The method for targeting frequency determines the percent number of corrected expression vectors compared to mutant expression vectors. The number of corrected plasmids is determined by transforming bacteria with expression vector isolated from the nucleus of cells and growing the bacteria on plates the appropriate with selection or substrate. The total number of plasmids is determined by growing the bacteria on plates with ampicillin. The percent number is determined by dividing the number of colonies that grow on the appropriate selection or substrate plates divided by the number of colonies that grow on ampicillin plates.

I. Expression Vector System and Method for Assessment of DNA Nuclear Delivery and Quantification of Targeting Frequency Expression vector system comprising a pair of expression vectors constructed from a wild-type and a mutant version of any marker reporter, or selection gene is useful in a method for assessment of DNA nuclear delivery and quantification of targeting frequency. The assessment includes optimization of the DNA delivery efficiency of the DNA delivery, confirmation of the DNA delivery, confirmation of gene targeting, assessment of cell enzymatic function and cell enzymatic pathways.

Cell enzymatic function and cell enzymatic pathways are assessed when cells are transfected with the mutant version of the expression vector. If the vector is corrected, then enzymatic function and pathways are active. If the vector is not corrected, then enzymatic function required for homologous replacement and pathways are either disrupted by the transfection vehicle or they are not functioning.

The method is performed in cells that are submitted to genetic manipulation such as gene targeting and gene therapy, and is especially useful for assessment of nuclear delivery and efficiency of such delivery and quantification of targeting frequency of small fragment homologous replacement (SFHR). SFHR has been recently successfully used to correct gene defects. However its targeting frequency was, until this invention, difficult to determine for lack of precise assessment and quantitative methods. The current invention provides such methods.

A. Expression Vector System

Expression vector system consists, in its broader scope, of a pair of wild-type and mutant version of any reporter or selection gene.

1. Marker Genes

Marker gene means any gene which is not expressed in the cell and which is detectable by enzymatic, isotopic, chemiluminescent, bioluminescent, ELISA, in situ visualization, calorimetric, fluorescence or cell survival assays. Examples of the marker genes are reporters or selection genes and any other gene falling within the marker gene definition.

2. Selectable Genes

Selectable genes, also called selectable marker genes, are essential for genetically modified organisms. Selectable genes are easy to detect and are therefore often used to tag the genes of interest. Typically, these genes confer resistance or tolerance to an organism expressing or by overexpressing protein molecules sensitive to a selective agent.

For purposes of this invention, the wild-type of any one of these genes in their dysfunctional form, is used to prepare a vector comprising that gene and to transfect the cells with that vector. The method for vector construction is described in Example 2. The number of functional vectors that is found in the cell nucleus determines the transfection efficiency. In the same way, the mutant vector of the same selectable gene is prepared, as described in Example 2 or using other methods such as site directed mutagenesis. The mutant vector is also used to transfect the genetically modified cells where the determination of genetic correction is to be made.

Selectable genes are, among others, aminoglycoside phosphotransferase II gene (neo G418, APH), hygromycin-B-phosphotransferase gene (hygr), bleomycin resistance gene (bleo), zeocin gene (zeo), sulfonamide resistance gene (sull), hypoxantine phosphoribosyl transferase gene (HPRT), adenine phosphoribosyl transferase gene (APRT), adenosine deaminase gene (ADA), cytosine deaminase gene (CDA), dihydrofolate reductase gene (DHFR), histidinol dehydrogenase gene (hisD), puromycin-N-acetyl transferase gene (PAC), thymidine kinase gene (TK), xanthine-guanine phosphoribosyltransferase gene (gpt), diphtheria toxin gene (DT) and herpes simplex virus thymidine kinase gene (HSV-TK); and other selectable genes known now or those which will become known in the future. List of selectable and reporter genes is found, for example, in *BioTechniques,* 29:314 (2000) and *Mol. Biotechnol.,* 13:29 (1999).

3. Reporter Genes

Reporter genes are genes which are not endogenously expressed in the cell types and can be used to evaluate another gene or regulatory element. These genes are also easy to monitor and detect.

Reporter genes are, among others, chloramphenicol acetyl transferase gene (CAT), β-galactosidase gene (β-gal), luciferase gene (luc), alkaline phosphatase gene (AP), secreted alkaline phosphatase gene (SEAP), β-glucuronidase gene (GUS), green fluorescent protein gene (GFP), human growth hormone gene (hGH) and β-lactamase gene (β-lac), and other reporter genes known now or those which will become known in the future. List of selectable and reporter genes is found, for example, in *BioTechniques,* 29:314 (2000) and *Mol. Biotechnol.,* 13:29 (1999).

4. Expression Vectors

Vectors suitable to be used for the current invention are numerous and a list of the vectors can be found in the art. The vectors commercially available from Stratagene, Promega, CLONTECH, Invitrogen GIBCO Life Sciences and other companies making expression vectors.

Vectors particularly suitable are plasmid vectors which include prokaryotic, eukaryotic and viral sequences. A list of these vectors can be found in *Gene Transfer and Gene Expression: A Laboratory Manual,* Ed. Kriegler, M., Stockton Press, New York (1990) and *Molecular Cloning,* A Laboratory Manual, CSH Laboratory Press, Cold Spring Harbor, N.Y. and *Current Protocols in Molecular Biology,* Vol. 1, Supplement 29, section 9.66, Ed. Asubel, F. M. et al., John Wiley & Sons (2001).

a. Wild-Type Plasmid Vector

Construction of wild-type plasmid vector is described generally in Example 2. All other plasmid vectors may be prepared in essentially the same way.

Typically, a selectable or reporter gene is introduced into the multiple cloning site of an expression vector under the control of two promoters: one that functions to express the gene in prokaryotic systems and one that expresses the gene in eukaryotic systems. Example of a promoter that functions in prokaryotic systems is EM-7. Examples of promoters that function in eukaryotic systems are cytomegalovirus (CMV), rous sarcoma virus long terminal repeats (RSV-LTR) and other promoters known in the art or as will become known in the future.

b. Mutant Version Vector

Mutant version of the wild-type vector prepared above may be prepared by the procedure described in Example 2 for zeocin.

Additionally, the mutation may be introduced by site directed mutagenesis as generally described in *The Scientist*, 15(3):25 (2001).

Site directed mutagenesis is performed, for example, by using kits to mutate genes in vectors, such as those obtained from Amersham, Bio-Rad, CLONTECH, 5 Primer[3] Prime, PanVera, Pharmacia, Altered Sites II, GeneEditor, Quantum Biotechnology, Stratagene, New England Biolabs, or by cassette insertion using a kit obtained from New England Biolabs, or by Interchange In Vivo Amber suppression obtained from Promega, and by following manufacturer's instruction.

The following is a list of oligonucleotide-directed mutagenesis kits commercially available. Not all site-directed mutagenesis kits are oligonucleotide based and the last two kits offer an alternative to oligo-directed mutagenesis. All these kits and other methods known in the art are intended to be within the scope of this invention.

Site-directed mutagenesis method is described in great details in Example 2. Other mutated vectors are prepared in the same manner or by using any of the methods described below and available commercially.

The pZamp vector described in Example 2 is mutated into the pZamp+4 vector using the Amersham Sculptor kit, for example. In order to do this, an oligo (21 nucleotides) containing the desired mutation in bold (acgaagtcccggccgggagaa: SEQ ID NO: 12) are first synthesized. The pZamp vector is incubated with the oligo so that they anneal and then extension of the oligo is performed with Ti polymerase in the presence of dCTP-S. After extension, the resulting heteroduplex is nicked in the non-thio containing, nonmutated strand with Nd II and then the nicked strand is removed with T5 exonuclease. The resulting single-stranded vector is rendered double-stranded by polymerization with pol I and DNA ligase. This double-stranded expression vector now contains the desired mutation.

Amersham Sculptor IVM Mutagenesis Kit relies on the inability of certain restriction enzymes to cut a DNA strand at a thionucleotide position. After annealing of user-supplied oligos bearing the desired alteration, extension with T7 polymerase is conducted in the presence of dCTP-S. The resulting heteroduplex is nicked in the non-thio containing, nonmutated strand with an enzyme that is sensitive to the presence of thionucleotides, such as Nc1 II. Following digestion with exo III to create gaps in the nicked, nonmutated strand, T5 exonuclease is brought in to remove the gapped strand. Mutant homoduplexes are made in vitro by final polymerization with pol I and DNA ligase. The whole mutagenesis is done in one day and in one tube and requires no special vectors or host cells. Replacing Klenow with T7 polymerase in the initial extension reaction increases the rate of the reaction and the ability to read through difficult regions. This enzyme avoids loss of mutation due to displacement by newly synthesized DNA. In addition, by using T5 exonuclease to remove unwanted single-stranded templates, template requirement is reduced from 5 to 2 µg of DNA. The kit comes with all necessary enzymes and buffers, dNTP mixtures, host cells, and a control mutant oligo and template.

Bio-Rad's Muta-Gene Mutagenesis Kit is based on the fact that uracil-substituted DNA can be selected against certain strains of bacteria. Uracil-substituted template can be prepared by growing vector in a strain of bacteria that carries two mutations in uracil metabolism, dut- and ung-, which together result in the substitution of uracil for thymine. When such a template is used in the mutagenesis process, and transformed into an ung+ strain of bacteria, the parental, uracil-containing strand is not replicated, leading to the efficient production of mutant containing plasmid. This kit is available either with a single-stranded vector (M13) or a double-stranded phagemid vector. The original version of the kit contains T4 polymerase and gene 32 protein. A newer version of the kit is available with T7 polymerase, which provides a more rapid rate of polymerization and is less likely to terminate prematurely at a region of secondary structure. Included in the kits are enzymes, buffers, hos strains and a set of control template and primers.

CLONTECH Transformer™ Site-Directed Mutagenesis Kit is based on the unique site elimination method (USE). Specific mutations are introduced into a target gene cloned into any double-stranded plasmid with a unique restriction site and a bacterial selection marker. Two primers are required: one to introduce the desired mutation and one to mutate the unique restriction site in the plasmid to a different restriction enzyme or to eliminate the unique site. Elongation by T4 DNA polymerase results in the incorporation of both mutations in the same newly synthesized strand. The double-stranded plasmid is digested with a restriction enzyme corresponding to the original unique site, removing all nonmutated plasmid. The DNA is then used to transform *E. coli* BMH 71-18 mutS, which is repair deficient and will propagate the mutated plasmids. A second round of transformation after redigestion of isolated DNA leads to a very high frequency of mutation in the final transformation reaction. The kit comes with the host cells, enzymes and buffers, and control template and primers.

5 Prime→3 Prime Morph Site-Directed Mutagenesis Kit relies on the resistance of hemi-methylated but not fully methylated DNA to digestion by the restriction enzyme, Dpn I. Virtually any double-stranded plasmid DNA containing the target sequence of interest can be specifically mutated without use of vector-specific selection or modification oligonucleotides. Target template is propagated in a dam+ bacterial strain, purified and then annealed with one or more user-supplied oligos bearing the mutation(s). Elongation from the oligo(s) by T4 DNA polymerase in vitro results in hemi-methylated, double-stranded, half-mutant plasmids that resist digestion with Dpn I whereas the fully methylated, non-mutant plasmids succumb to digestion. Transformation into repair deficient (nuts) bacteria yields up to 80% mutant plasmid-containing colonies. The kit comes with all enzymes, reagents and competent MORPH nuts cells.

PanVera's Mutant Super Express Km Kit uses PCR amplification and oligo-directed, dual-amber method for isolating mutants. In this procedure, the vector pKF 18k/19k, which has dual mutations in a kanamycin-resistance gene is grown up in a supE strain of bacteria. After cloning the target gene into this vector, mutagenesis of the target and reversion of the amber mutations in the kan gene are performed simultaneously using a mutagenic oligonucleotide and kan selection primer. *E. coli* that are transformed with the mutated plasmid, and selection for kanamycin resistance is performed.

Pharmacia Biotech Unique Site Elimination (USE) Mutagenesis Kit uses the unique site elimination method. Pharmacia's USE Mutagenesis Kit comes with FPLCpure T4 DNA polymerase and FPLCpure T4 DNA ligase, along with preformulated reactions and nucleotide mixes. Two sets of USE Selection/Toggle Primers are available separately, which can be used on most pUC or pHE-derived plasmids. One primer converts the Sca I site in the ampicillin-resistance gene to a Mlu I site. Another selection primer modifies the Ssp I site into a Stu I site. Neither mutation affects ampicillin resistance or plasmid function. Corresponding toggle primers can be used to reinstate the original sites and enable successive rounds of mutagenesis. Also available separately are pGEX USE primers that allow the rapid mutagenesis of DNA inserts that are cloned into any of the pGEX series of bacterial expression vectors. When used with USE Mutagenesis Kit, the primer sets enable a series of site-specific mutations to be successively incorporated into cloned gene sequences without subcloning.

Altered Sites II In Vitro Mutagenesis Systems introduce mutations into DNA using a dual primer system to simultaneously create site-directed mutations and antibiotic resistance. There are three systems that differ in the vector: pALTER-1 is the original vector; pALTER-Ex-1, and Ex-2, which contain translation initiation codons and ribosome binding Sites, allow in vivo and in vitro expression of mutated proteins. The pALTER and pALTER1 are ampicillin-sensitive. The ampicillin repair oligonucleotide provided is used to convert the vectors to ampicillin resistance in the same reaction in which the cloned insert is mutated. The pALTER-Ex-2 is chloramphenicol sensitive, and is converted to chloramphenicol resistance during the mutagenesis reaction. Screening for antibiotic resistance is a positive selection for the mutant strand.

The Altered Sites Mammalian Mutagenesis system uses the same principle as the Altered Sites Directed Mutagenesis System with a mammalian expression/mutagenesis vector. This vector is based on pCI-Neo and is both ampicillin sensitive and chloramphenicol resistant. A mutagenic oligo is used to convert the plasmid to ampicillin-resistance in the sane reaction in which the cloned insert is mutated, supplying a positive selection for mutated plasmid.

GeneEditor In Vitro Site-Directed Mutagenesis System achieves mutagenesis by coupling selection for the desired mutation to the positive selection for a new antibiotic resistance. Any vector with an ampicillin-resistance gene can be used in this system. Positive selection for mutants occurs by altering the ampicillin-resistance gene in a vector to confer resistance to the GeneEditor Antibiotic Selection Mix. Synthesis of the mutant strand links the desired mutagenic oligonucleotides and the provided antibiotic-resistance selection oligonucleotide. Under these conditions, only mutants grow, minimizing the screening required. The GeneEditor System can be used for large insertions or deletions and multiple, simultaneous mutations. All reagents required are provided, including competent cells.

The Quant-Essential Kit obtained commercially from Quantum Biotechnologies is based on a closing oligonucleotide that is used in conjunction with a user-specified mutagenic oligonucleotide. Following linearization within the ampicillin resistance gene of uracilated plasmid, the mutagenic primer is annealed to the template. The closing oligonucleotide is used to recircularize the same strand of the template, and elongation by T7 DNA polymerase results in incorporation of both primers into the same non-uracilated strand. The completed double-stranded plasmid is transformed into ung+ bacteria, resulting in dual selection. The first selection is based on the fact that only plasmids that have been recircularized with the closing oligo and extended by T7 DNA polymerase will transform bacteria. The second selection utilizes the fact that the mutagenized non-uracilated strands are preferentially replicated in ung+ bacteria. Using this method, insertions, deletions and point mutations can be generated. The kit comes with dut, ung and dut+ bacterial strains, positive control plasmid and primer, and T7 polymerase.

The Stratagene QuickChange Mutagenesis Kit uses double-stranded DNA and two synthetic oligonucleotide primers containing the desired mutation. The oligo primers, each complementary to opposite strands of the vector are extended during temperature cycling by Pfu DNA polymerase. Temperature cycling generates copies of the plasmid by linear amplification, incorporating the mutation of interest. Primers are designed so that they can only extend on the parental strands, disallowing re-amplification and possible error generation in the mutant strand. Digestion with Dpn I removes all pure parental DNA templates (DNA isolated from almost all *E. coli* strains is dam methylated and therefore susceptible to digestion by Dpn I cleavage). The kit comes with two enzymes, Pfu DNA polymerase and Dpn I, competent XL-2 Blue cells, as well as whitescript plasmid and two mutagenic primers that restore the beta-gal gene, for a positive control.

Stratagene Site PCR-Based Site-Directed Mutagenesis Kit protocol uses PCR with a set of mutagenic primers, followed by digestion of the heteroduplex with Dpn I to eliminate in vivo methylated parental templates. Using increased template concentrations keeps the cycle number down to less than 10. With appropriate primers, deletions and insertions as well as point mutations can be introduced into genes on plasmids. The kit comes with TaqPlus Long PCR system, cloned Pfu DNA polymerase, Dpn I and control oligonucleotides.

The Stratagene Chameleon Double-Stranded Site-Directed Mutagenesis Kit applies a modification of the unique-site elimination method in which mutagenic primers are used to alter restriction sites within antibiotic resistance genes. This allows for the selective digestion of the nonmutated plasmid. Switch primers are also provided to allow a second round of mutagenesis to recreate the original unique restriction site. The kit comes with selection primers, mutageneic primers for pBluescript II phagemid-competent cells, and enzymes and buffers.

In alternative to oligo-directed mutagenesis, the mutated version vector may be prepared using New England BioLabs Code 20 Kit or by Promega.

New England Biolabs Code 20 kit provides a means of inserting any one of the 20 amino-acid codons at specific sites in DNA using universal mutagenic cassettes. A target molecule lacking a Sap I site must be constructed with a blunt, double-stranded break at the site for mutagenesis.

Double-stranded mutagenic codon cassettes, which are three-base pair, direct-terminal repeats with two head-to-head recognition sites for Sap I, are inserted at the target site by ligation. This plasmid molecule containing the cassette is then digested with Sap I, thereby removing most of the cassette, except for a three-base, cohesive extension that is then ligated to create the final insertion or substitution mutation. Each kit comes with 11 double-stranded cassettes, pLITMUS 28, a polylinker vector with no Sap I restriction sites, Sap I enzyme and buffer and enough reagents for 20 amino acid substitutions at 10 different positions. This method does not require a mutagenic oligo, but does require that there be an appropriately positioned restriction site in the gene of interest.

Another kit which is useful for preparation of mutated version vector is commercially available from Promega.

Promega kit is a collection of 12 amber suppressor-containing *E. coli*, with which it is possible to insert one of 12 amino acids at the site of an amber-stop codon in a gene sequence. This approach allows for the study of the effect of up to 12 amino acids in the same site. Five of the suppressors are derived from chromosomal mutations and the remainder are synthetic constructs on ColE1 plasmids. Any vector can be used with the chromosomal-based suppressors, but pACYC184, supplied with the kit, or others containing an alternate origin of replication, must be used with the plasmid-based suppressors. The strains also contain a chromosomal amber mutation in the arginine biosynthetic pathway which allows selection for the suppression activity by plating on minimal medium. All the *E. coli* strains are supplied as competent cells with an efficiency of at least 103 cfu/ug DNA.

Using these and other techniques suitable for introduction of the mutation, any wild-type reporter or selectable gene may be mutated to obtain its mutated version by insertion or deletion of DNA short fragment(s). In addition, any other marker gen may be suitably utilized in the current invention as long as it possesses properties described above for selectable or reporter genes.

A final example for site-directed mutagenesis is a technique that is performed in bacteria. In this technique, the vector pZamp can be mutated to the pZamp+4 vector by transforming the pZamp vector into bacteria along with a double-stranded short piece of DNA that contains the desired mutation (acgaagtcccggccgggagaa). The bacteria are able to mitigate homologous recombination between the vector and the short piece of DNA and the resulting product is a mixture of pZamp and pZamp+4 vectors. The bacteria are plated onto LB plates containing ampicillin and colonies are picked to be screened for the desired mutant vector.

These and all other methods known in the art used for preparation of mutants may be used to prepare mutant version vector. Plasmid vector is preferably purified before bacterial transformation by gel, ultracentrifugation of plasmid in a CsCl gradient followed by ethanol precipitation, according to *Biotechniques,* 26:1056 (1999) and *Current Protocols in Molecular Biology*, Supplement 29, section 9.6.6. (Supra), or by any other method suitable for such purposes.

Another purification method is by ultracentrifugation of plasmid in a CsCl gradient followed by ethanol precipitation according to *BioTechniques* 26:1056–1060 (1999).

B. Assessment of DNA Nuclear Delivery and Quantification of Targeting Frequency

A method for assessment of DNA nuclear delivery or for quantification of targeting frequency is useful for such assessment or quantification in cells or tissue previously subjected or to be subjected to targeted DNA delivery and/or gene therapy where the results of such DNA delivery need to be confirmed and/or quantified. Confirmation provides evidence that the DNA was transferred or delivered to a site where it was supposed to be delivered. Quantification provides evidence as to how efficient such delivery was, that is, what the frequency of targeting was. Typically quantification is expressed as percentage.

For confirmation of DNA delivery or quantification of targeting frequency, cells are transfected with either the wild-type vector or with the mutant version thereof according to the co-transfection on protocol described in Example 4 under conditions that modulate SFHR-mediated correction of a defective gene. These conditions include evaluation of various delivery system, such as cationic lipid, anionic lipid, cationic polymer, electroporation, and microinjection, varying plasmid to fragment ratio by varying the amount of plasmid to fragment, varying fragment length between about 300 to about 1000 bp, fragment strandedness (single or double stranded DNA) and such other conditions as may become important for SFHR modulation. These and other conditions are described in *BioTechniques,* 29:314 (2000), incorporated by reference.

To determine exact conditions for each type of investigated cells is within the skills of artisan given the general description herein of the method for determination of such conditions.

1. Transfection Efficiency

For determination of transfection efficiency investigated cells are transfected with the wild-type vector, comprising either the selectable or reporter gene as described above, using any transfection vehicle and delivery system as described above. Then the nuclear and whole cell lysates are isolated and the vector is extracted from each of the lysate and from the nuclear fraction. The isolated vector is used for bacterial transformation. Detailed description of this process is given in Example 6.

Bacteria, such as DH5α, JM109, DH10B are transformed using electroporation or heat shock or other such techniques known in the art suitable for these purposes with the isolated vectors under conditions essentially described in Example 6.

Typically, after about 1–2 hours of incubation at about 37° C., aliquots of transformed bacteria are spread in duplicate onto agarose L-Broth plates. One plate contains ampicillin and the other plate contains the appropriate selection antibiotic or substrate such as zeocin or neomycin.

The culture is again incubated, preferably overnight at about 37° C., then the colonies are counted and targeting frequency is determined from the difference between the nuclear lysate and whole cell lysate.

The frequency of correction is defined as the number of colonies that have grown on the ampicillin plate divided by the number of colonies that have grown on the selection antibiotic or substrate plate.

The assay plate may also be analyzed by staining with a stain or calorimetric fluorescent dye and visually identified or colorimetry is used or, in the alternative, bacteria are contacted with an appropriate antibody and the number of colonies are determined.

II. Confirmation, Evaluation and Optimization of DNA Delivery

Confirmation, evaluation and optimization of DNA delivery, particularly for SFHR was investigated by molecular characterization of transient transfection, and by molecular characterization of stable transfection.

The frequency of SFHR-mediated correction was used as a means to evaluate the above described method and determine those conditions that can enhance the effectiveness of SFHR in human epithelial cells.

For this purpose, the defective zeocin™ antibiotic resistance gene (zeo$^r$), in a prokaryotic/eukaryotic expression vector described in greater detail below, was co-transfected with small fragments of wild-type zeo$^r$ DNA into transformed CF airway epithelial cells. SFHR-mediated correction was determined as restoration of zeocin-resistance after transient transfection and stable transfections in eukaryotic, specifically human epithelial cells. In addition, both prokaryotic and eukaryotic zeocin resistant clones were characterized by restriction enzyme digestions, direct DNA sequencing and Southern blot hybridization.

The conditions that modulate SFHR-medicated correction of a defective Zeocin™ antibiotic resistance (zeo$^r$) gene that has been inactivated by a 4-bp insertion were also evaluated. The conditions include delivery systems, plasmid to fragment ratio, fragment length and fragment strandedness (single or double stranded DNA). Targeting fragments which were used, comprised the wild-type $zeo^r$ gene sequence and were either 410-bp for fragment Zeo 1, or 458-bp for fragment Zeo 3.

Expression vectors containing the corrected $zeo^r$ gene were isolated as episomal plasmids or were allowed to stably integrate in cultured human airway epithelial cells. Correction of the $zeo^r$ gene was phenotypically defined as restoration of resistance to zeocin in either bacteria or in epithelial cell clones.

Extrachromosomal gene correction was assayed using polymerase chain reaction (PCR) amplification, restriction enzyme digestion, DNA sequencing and Southern blot hybridization analysis of DNA from isolated prokaryotic and eukaryotic clones. Neither random sequence alteration in the target episomal gene nor random integration of the small fragments was detected. Targeted correction efficiencies of up to 4% were attained.

The description of procedures used in these studies provide directions for those skilled in the art how to use the current invention. Parameters and conditions need to be modulated for the optimization of SFHR-mediated targeting. However, given the directions described herein, such parameters and conditions are easily determined for each reporter or selectable gene.

A. Expression Vector Pairs

For a method of confirmation and evaluation of DNA delivery during SFHR and for determination of optimal conditions for such delivery, an expression vector or preferably a pair of expression vectors was developed.

The pairs of the expression vectors suitable for confirmation, evaluation and optimization of DNA delivery, were constructed, in the most general terms, from a wild-type and from the mutant version of any reporter or selection gene, as described above.

Specifically, as already described above, one such pair comprised a wild type and the mutant version of zeocin-resistant gene ($zeo^r$). Vector pZamp containing a wild type, functional copy of the $zeo^r$ gene and the mutant version thereof, namely the vector pZamp+4, contained the mutant nonfunctional copy of the $zeo^r$ gene were constructed, as seen in FIG. 1 for pZamp+4.

FIG. 1 is a schematic representation of the defective plasmid (pZamp+4), replacement fragments and primer locations. The defective plasmid differs from the normal plasmid (pZamp) by the addition of 4-bp in the $zeo^r$ coding sequence. The Zeo1 fragment (410-bp) starts 33-bp downstream of the ATG codon of the $zeo^r$ gene and ends 71-bp downstream of the stop codon. The Zeo3 fragment (458-bp) starts 13-bp upstream of the ATG codon. Forward (Z1, Z1Bss, Z3) and revers (Z2, Z4) primers are indicated.

The vector pZamp was developed by the introduction of the ampicillin resistance (ampr) gene (fragment SalI-PvuII) from pcDNA3 into the multiple cloning site (XhoI-PvuII) of pZeoSV where the pZeoSV vector contains the $zeo^r$ gene under CMV eukaryotic and EM-7 prokaryotic promoters.

The vector pZamp+4 was developed, as seen in FIG. 1, by linearizing the pZamp vector at a unique XmaI restriction cleavage site within the $zeo^r$ gene coding sequence, wherein the linearized vector is incubated with Klenow enzyme to fill in the overlapping bases and then ligated and wherein the pZamp+4 vector carries a 4-bp insertion that eliminates the XmaI restriction site and is not resistant to the zeocin antibiotic in either prokaryotic or eukaryotic cells.

B. Molecular Characterization of Transient Transfection

Targeting frequency was determined from the transient transfection experiments. However, the accuracy of this measurement was dependent on the purification protocol. Due to the residual contaminating fragments present in all cell lysates which is seen in FIG. 2, it was necessary to gel purify extracted plasmid from the lysates before bacterial transformation.

Agarose gel analysis of cell lysates also indicated that linear plasmid and genomic DNA were absent and that the extracted plasmid was either in a supercoiled or relaxed form. Estimates based on comparison to a mass ladder indicated a plasmid recovery between 1–2% of the total plasmid DNA transfected.

Figure 2:
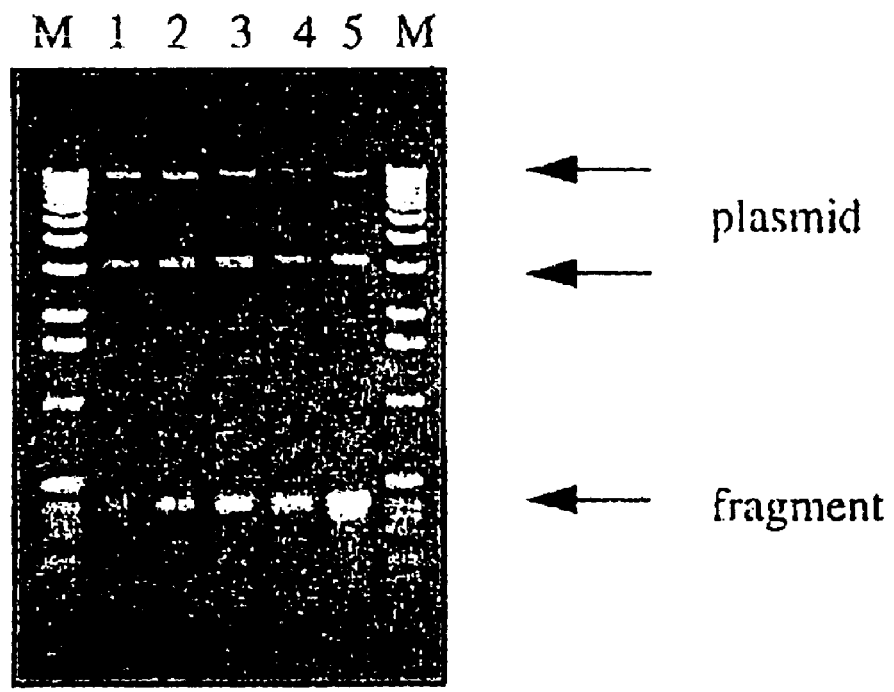
FIG. 2 depicts electrophoretic analysis of plasmid DNA from the total cell lysate following DOTAP or SuperFech transfection.

Exploring different conditions for optimization of the method is seen in FIG. 2 where the different ratios of plasmid to fragment is shown.

FIG. 2 is an electrophoretic analysis of plasmid DNA from the total cell lysate following DOTAP or SuperFect transfection. The molecular weight marker (1 kb ladder) is in the M lanes. Lanes 1–5 represent the lysate from separate transfections with different plasmid to fragment ratios, specifically 1:2 (lane 1), 1:5 (lane 2), 1:10 (lane 3), 1:30 (lane 4), 1:60 (lane 5), respectively. The upper side arrows indicate the relaxed and supercoiled forms of the plasmid DNA, respectively, and the lower side arrow indicates residual targeting fragment present in the cell lysate.

One factor defining a eukaryotic expression vector system is whether the expression is transient or stable. Transient expression systems are particularly useful for evaluation of elements which regulate gene expression, evaluation of the efficiency of DNA delivery and/or evaluation of gene targeting. Additionally, they provide this information in a short time frame.

Transient expression is predicated on a burst of gene expression occurring between 12 and 72 hours and can be evaluated, for example, in terms of the protein produced in the transfected cells such as the activity of a reporter or selectable gene that is not normally present in the cell type used.

Transient expression studies were performed to evaluation SFHR-mediated correction of a mutant zeocin gene expression. Results are described in FIG. 3.

Molecular analysis following transient transfection with pZamp+4 and Zeo1 fragments is seen in FIG. 3. FIG. 3A illustrates XmaI digestion analysis of plasmid DNA isolated from $zeo^r$ bacterial clones. Lanes M show molecular weight marker (1-kb ladder); lanes 1–12 show zeo1 clones (corrected plasmid); lane 13 shows defective plasmid (pZamp+4) control. FIG. 3B illustrates XmaI digestion analysis of PCR products (primers Z1 and Z4). Lanes M show molecular weight marker (123-bp ladder); lanes 1–10 show $zeo^r$ clones (corrected plasmid); lane 11 shows defective plasmid (pZamp+4) control. FIG. 3C shows direct sequence analysis of the defective plasmid (pZamp+4) and an SFHR-corrected $zeo^r$ clone. Bold letters indicate the 4-bp insertion in the pZamp+4 plasmid that subsequently disrupts the XmaI cleavage site.

Figure 3A:
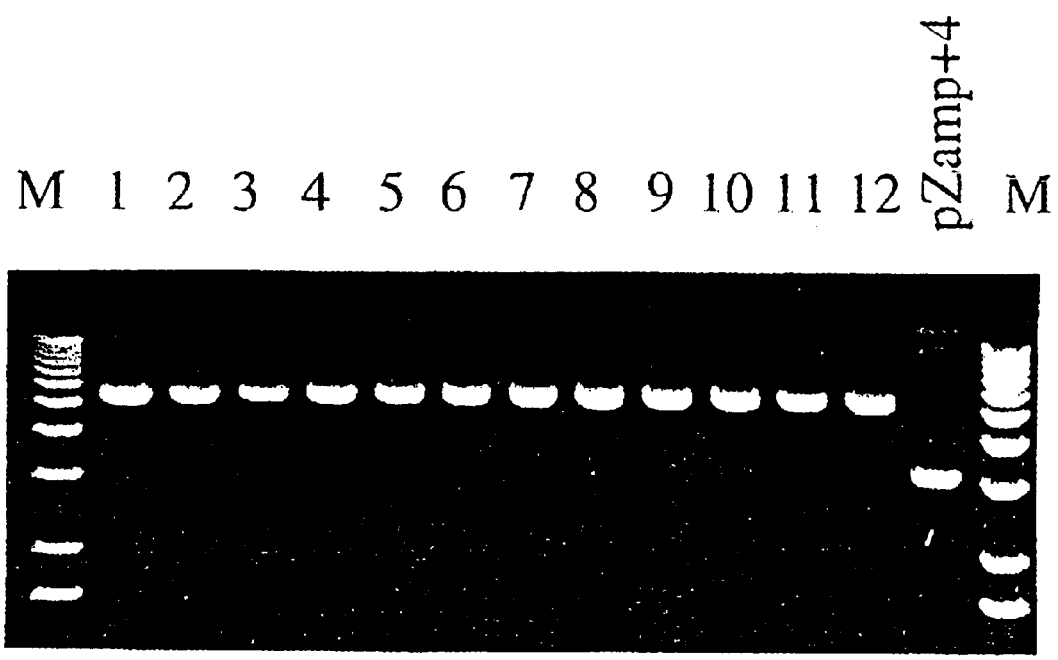
FIG. 3A shows XmaI digestion analysis of plasmid DNA isolated from zeo$^r$ bacterial clones.
Figure 3B:
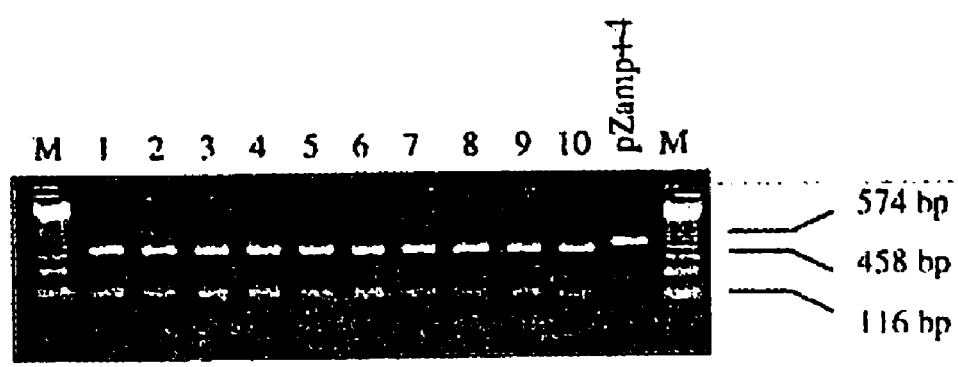
FIG. 3B shows XmaI digestion analysis of PCR products using Z1 and Z4 primers.
Figure 3C:
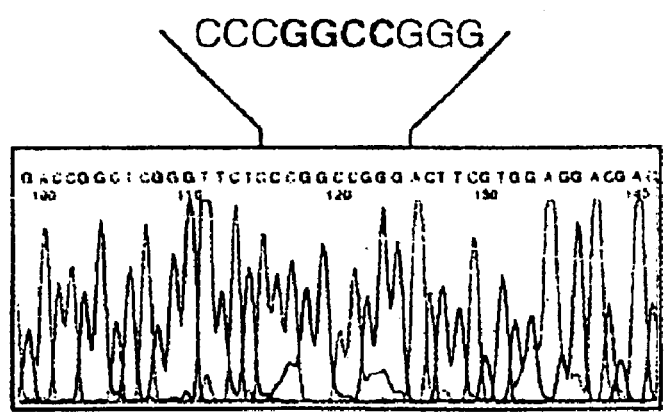
FIG. 3C is a direct sequence analysis of the defective plasmid pZamp+4 (SEQ ID NO: 10) and an SFHR corrected zeo$^r$ clone (SEQ ID NO: 11).
Figure 3C:
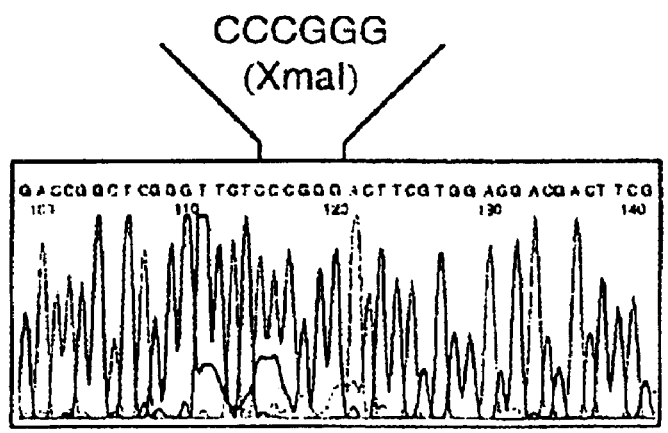

The presence of an intact $zeo^r$ gene in the extracted plasmids was indicated by the cleavage of plasmid DNA with XmaI, seen in FIG. 3A, showing restoration of the wild type sequences in the mutant pZamp+4 plasmid. Correction was also verified through XmaI digestion of the PCR product after amplification of the plasmid DNA with $zeo^r$-specific primers, seen in FIG. 3B. Only plasmid isolated from $zeo^r$ bacterial clones showed the expected 458- and 116-bp bands. Finally, the $zeo^r$ gene in 10 randomly chosen $zeo^r$ bacterial colonies was sequenced in both directions. Removal of the 4-nt insertional mutation was observed in each case, seen in FIG. 3C, and no additional sequence alterations were detected along the entire $zeo^r$ gene.

Correction frequency of supercoiled DNA is shown in Table 1.

TABLE 1

Supercoiled DNA Correction Frequency

| Gene Delivery System | Fragment type | Plasmid: Fragment | Targeting Frequency (n = 3) | Standard Deviation |
|---|---|---|---|---|
| DOTAP | ssZeol | 1:5 | $2.37 \times 10^{-5}$ | $0.87 \times 10^{-5}$ |
| | | 1:10 | $4.93 \times 10^{-5}$ | $0.82 \times 10^{-5}$ |
| | | 1:30 | $2.70 \times 10^{-5}$ | $0.29 \times 10^{-5}$ |
| | dsZeol | 1:5 | $4.93 \times 10^{-5}$ | $1.39 \times 10^{-5}$ |
| | | 1:10 | $3.57 \times 10^{-5}$ | $1.33 \times 10^{-5}$ |
| | none | | 0 | 0 |
| SuperFect | ssZeol | 1:5 | $5.93 \times 10^{-5}$ | $1.59 \times 10^{-5}$ |
| | | 1:10 | $2.33 \times 10^{-5}$ | $0.68 \times 10^{-5}$ |
| | | 1:30 | $2.50 \times 10^{-5}$ | $1.30 \times 10^{-5}$ |
| | | 1:50 | $2.73 \times 10^{-5}$ | $1.91 \times 10^{-5}$ |
| | | 1:60 | $7.10 \times 10^{-5}$ | $1.42 \times 10^{-5}$ |
| | dsZeol | 1:5 | $4.47 \times 10^{-5}$ | $1.35 \times 10^{-5}$ |
| | | 1:10 | $4.63 \times 10^{-5}$ | $0.76 \times 10^{-5}$ |
| | none | | 0 | 0 |
| Electroporation | ssZeol | 1:10 | $2.75 \times 10^{-3}$ | $0.42 \times 10^{-3}$ |
| | | 1:100 | $1.17 \times 10^{-2}$ | $0.24 \times 10^{-2}$ |
| | dsZeol | 1:10 | $1.17 \times 10^{-2}$ | $0.09 \times 10^{-2}$ |
| | ssZeo3 | 1:10 | $4.07 \times 10^{-2}$ | $0.68 \times 10^{-2}$ |
| | none | | 0 | 0 |

SFHR-mediated correction of supercoiled episomal pZamp + 4 vector after transient transfections with replacement DNA fragements.
ss = single-stranded fragment
ds = double stranded fragment Following transfection of cells with DNA-DOTAP or DNA-SuperFect complexes, targeting frequencies ranging from $1.0 \times 10^{-5}$ were observed and are listed in Table 1, rows 1–13. This frequency was independent of the time at which the plasmid was isolated, whether at 48 hours or 72 hours, after transfection. Neither bacterial mediated correction or spontaneous reversion was observed in Table 1, rows 6, 14, or 19.

In addition, targeting frequency appeared to be independent of the single or double stranded character of the fragment or of the plasmid to fragment molar ratio within the range tested. A dramatic 100- to 1000-fold improvement in SFHR efficiency was observed when cells were transfected by electroporation, seen in Table 1, rows 15–19. For example, a targeting frequency of ~0.3% was indicated using the ssZeo1 fragments at a plasmid to fragment molar ration of 1:10.

In subsequent SFHR studies, electroporation was used to further evaluate the effects of the plasmid to fragment ratio, fragment length and fragment strandedness (ss or dsDNA) on the targeting frequency. The frequency improved to $\geq 1\%$ (a five-fold improvement) with ssZeo1 fragments by increasing the plasmid to fragment molar ratio to 1:100. A comparable efficiency (~1%) was achieved when dsZeo1 fragments were used and the plasmid to fragment ratio was 1:10. The highest replacement frequency (4%) was observed with ssZeo3 fragments at a plasmid to fragment ration of 1:10.

A potential issue in using artificial vehicles for delivery is that the transfected DNA may be retained in endosomes and other cytoplasmic organelles and not be efficiently transferred into the nucleus as described in Curr. Opin. Mol. Ther., 1:140 (1999).

To test whether this was a factor in this invention, control studies with wild type pZamp vectors were carried out. The vector was transfected into cells either via artificial vehicles or by electroporation and then extracted from the cytoplasmic compartment after 48 hours. There were abundant amp$^r$ colonies present in the extract following transfection with artificial vehicle, whereas there were significantly fewer colonies in the extracts following electroporation. These results show that intact plasmid is retained in the cytoplasm and is probably protected from degradation after transfection with artificial vehicles. Thus, in this case, accurate assessment of the targeting frequency becomes compromised. In such a case, the total cell lysates contain amp$^r$, defective plasmid that has not entered the nucleus and has, therefore, not been accessible to the homologous replacement machinery.

To elaborate on this point, further studies were performed to determine the extent to which the assessment of targeting frequency could be influenced by the presence of cytoplasmic-plasmid. In these studies, total cell extracts were compared to nuclear extracts in terms of their relative targeting frequencies. The frequency increased a 100-fold in nuclear lysate when compared to the whole cell lysate from cells transfected with artificial vehicles, seen in Table 2. As seen in Table 2, there was no difference in frequency between the nuclear and total cell lysates of electroporated cells.

TABLE 2

Correction Frequency: Total Cell vs Nuclear Lysates

| Gene delivery system | Lysate | Fragment type | Targeting Frequency (n = 2) | Standard Deviation |
|---|---|---|---|---|
| DOTAP | Nuclear | ssZeol | $3.05 \times 10^{-3}$ | $0.95 \times 10^{-3}$ |
| | Total | | $1.55 \times 10^{-5}$ | $0.15 \times 10^{-5}$ |
| SuperFect | Nuclear | ssZeol | $2.35 \times 10^{-3}$ | $0.35 \times 10^{-3}$ |
| | total | | $2.45 \times 10^{-5}$ | $0.05 \times 10^{-5}$ |
| Electroporation | Nuclear | ssZeo3 | $4.25 \times 10^{-2}$ | $0.75 \times 10^{-2}$ |
| | Total | | $3.40 \times 10^{-2}$ | $0.20 \times 10^{-2}$ |

SFHR-mediated correction was determined from nuclear and total cell lysates after transient transfection with a 1:10 plasmid/fragment molar ratio.

The studies presented here demonstrate the sensitivity of the assay system and the SFHR conditions that lead to effective correction of the defect. A primary factor influencing the efficiency of SFHR-mediated correction appears to be the DNA delivery system. In the present study, electroporation was 1000-fold more effective for extrachromosomal gene targeting when compared to transfection with cationic liposome or dendrimer complexes.

Following electroporation, there was no significant difference in targeting frequency using plasmids isolated from the nuclear or the whole cell lysates. In addition, very few functional plasmids were detected in the cytoplasmic fraction 48 hours after electroporation.

The finding, in the electroporation experiments, that dsDNA fragments (dsZeo1) were 10-fold more efficient than the corresponding ssDNA fragments (ssZeo1) in facilitating homologous replacement when the plasmid to fragment ratio was 1:10, suggests that different enzymatic pathways mediate SFHR.

While the fragment to plasmid ratio appeared to have no dramatic effect in modifying the targeting frequency in cells transfected using artificial delivery vehicles, the studies using electroporation showed a 5-fold increase in targeting when the fragment to plasmid ratio was increased by 10-fold (ssZeo1 fragment). The results from the whole cell extract comparison clearly show that transfection with artificial vehicles is complicated by retention and protection of the DNA complex within the cytoplasm. For this reason, electroporation method is preferred and should be used as a standard delivery protocol to obtain measurement of how fragment to plasmid ratio influences targeting efficiency.

C. Molecular Characterization of Stable Transfection

Figure 4:
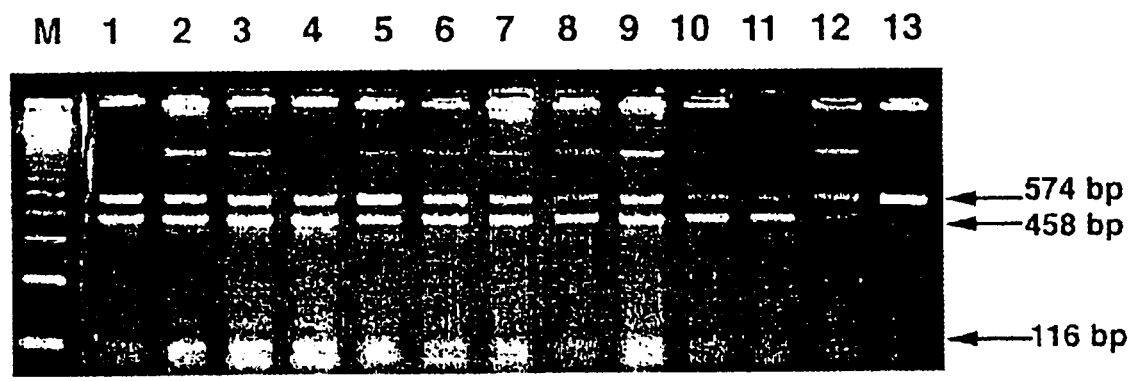
FIG. 4 depicts PCR and restriction enzyme analysis of 12 individual zeo$^r$ epithelial cell clones.

In parallel experiments using a plasmid to fragment (dsZeo1) ratio of 1:10, 20 unique zeo$^r$ epithelial cell clones were isolated by selection in zeocin containing media. The clones were selected after transfection of $4.8 \times 10^5$ cells with SuperFect. PCR amplification and restriction enzyme digestion (XmaI) of genomic DNA from the zeo$^r$ epithelial clones indicated that these clones contain at least one SFHR-corrected copy of the zeo$^r$ gene giving rise to a minimum correction frequency of $4.1 \times 10^{-5}$. Results are seen in FIG. 4. In addition, the XmaI digest of the PCR amplicons shows that both corrected and uncorrected copies of the gene-containing plasmids have integrated into the genomic DNA, because both uncut (574-bp) and cut (458- and 116-bp) products were present as seen in FIG. 4.

FIG. 4 shows PCR and restriction enzyme analysis of 12 individual zeo$^r$ epithelial cell clones. Total DNA was isolated from the cells, subject to PCR amplification with primers Z1 and Z4 (574-bp) and the amplicon was then digested with XmaI. Defective plasmid will not cut with XmaI (lane 13). Corrected plasmid will generate two bands, 458- and 116-bp. The presence of the 574-bp band in lanes 1–12 indicated that both corrected and uncorrected plasmid are present. Lane M was molecular weight marker (123-bp ladder).

Southern hybridization analysis of zeo$^r$ epithelial cell clones was then performed. Results are seen in FIG. 5.

Figure 5:
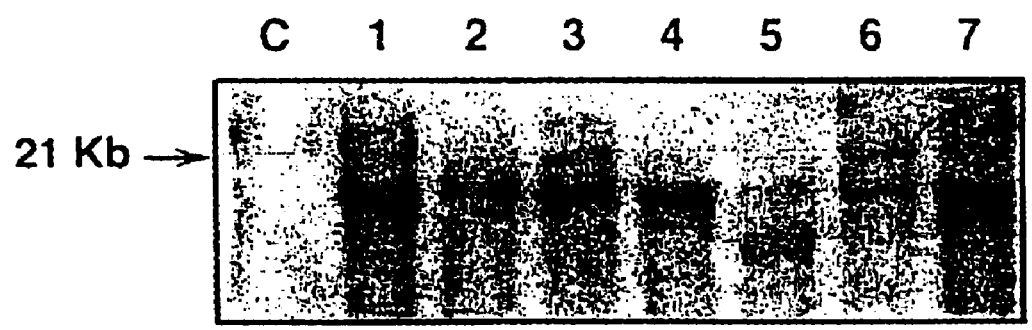
FIG. 5 is Southern blot hybridization analysis of 7 individual zeo$^r$ epithelial cell clones.

FIG. 5 illustrates Southern blot hybridization analysis of 7 individual zeo$^r$ epithelial cell clones. All the samples were digested with EcoRI, which is not present in either the pZamp or the pZamp+4 plasmids. Blots were hybridized with a zeo$^r$-specific probe. Lanes 1–7 are zeo$^r$ epithelial cell clones. Lane C is CFBE 41o$^-$ cell line used as control DNA.

Southern hybridization analysis, as seen in FIG. 5, showed several high-molecular weight bands in individual clones and indicated the integration of the plasmids into different genomic loci. The finding that the plasmid(s) has stable integration is further supported by the absence of bands representing the linear, supercoiled or relaxed forms of the plasmid. In addition, because the hybridization pattern using both CMV and Zeo1 probes were identical, it can be concluded that no random integration of the replacement fragments occurred. This pattern did not change even after the clones were propagated for more than 50 subcultures.

A consideration in using the transient transfection expression systems to obtain an accurate quantification of SFHR-mediated correction is the cDNA character of the reporter/selection marker genes used as targets. Because these assay systems are comprised of cDNA, no intron sequences are present in the replacement fragments. This could result in an underassessment of the targeting efficiency, because SFHR-mediated correction could introduce inactivating mutations into the coding region when the ends of the targeting fragments are within exons. Fortunately, the small size (374-bp) of the selection gene chosen in the zeocin system has facilitated some degree of elucidation of this possibility. Of the two different replacement fragments. Between Zeo1 and Zeo3, only Zeo3 has both 5, and 3' ends outside of the coding region of the Zeo1 gene. It is, thus, possible that having the ends of the fragment outside the coding region, and the placement of the modifying sequences in a more central position within the replacement fragment, results in an increase of the targeting frequency from 0.3 to 4%.

Finally, the selective nature of this assay system allows for the isolation of individual zeo1 epithelial cell clones. Southern hybridization analysis of these isogenic clonal cell populations showed a heritable integration of the plasmids for >50 subcultures. More importantly, this analysis revealed no random integration of the correcting fragment after SFHR, addressing a very relevant concern about the safety of SFHR-mediated gene targeting.

III. Evaluation of Efficiency of DNA Delivery

The method of the invention is suitable for determination and evaluation of efficiency of DNA delivery, for optimization of such delivery, and for quantitation of targeting frequency.

The efficiency of gene delivery can be ascertained and optimized using the mutated vector, as described in section I, here exemplarized by pZamp vector, and any DNA delivery system as described above. After optimization of the DNA delivery system for delivery into the nucleus, cells are transfected with the mutated vector, such as pZamp+4 vector using the selected DNA delivery system. Cells are then transfected with different gene targeting elements, such as, for example, triplex forming oligonucleotides, RNA-DNA fragments, short DNA-fragments or complementary plasmids. Vector is then isolated from the nuclear extract and used to transform bacteria as described above. The bacteria are plated onto LB plates containing the resistant gene, such as ampicillin, and/or both ampicillin and the gene of interest. The efficiency of gene targeting is the number of colonies comprising corrected vectors divided by the number of resistant gene colonies comprising total vectors.

Optimization of transfection is accomplished by varying the amount of an artificial delivery system relative to the amount of plasmid or for physical delivery systems, varying the amount of DNA. After transfection, the vector is isolated from both whole cell and nuclear extracts using, for example, a modified HIRT procedure described in *Gene Ther.*, 5:149 (1998). The vector isolated from the nuclear extract is compared to that from the whole cell extract by transforming and then plating bacteria onto plates containing the resistance gene. The relative proportion of vector that has been successfully transferred into the nucleus is determined by comparing the number of colonies from the nuclear extract to those from the whole cell extract.

In summary, the zeocin system has provided an effective means to accurately quantify and characterize SFHR-mediated correction. The findings of the present study have provided insight into the conditions that modulate SFHR and the pathways that underlie SFHR-mediated targeting. Varying the conditions relevant to SFHR, such as the delivery systems, and/or the length and character of the DNA fragments, has been shown to influence gene targeting and can be further optimized to improve the efficiency of SFHR. SFHR appears sequence independent and can simultaneously add or delete multiple nucleotides whether or not they are adjacent. Thus, SFHR can complement other gene targeting strategies that are either limited to specific sequences or to the number of bases that can be simultaneously modified.

EXAMPLE 1

Cells

This example describes SV40-transformed cells and procedure used for their growth and culturing.

SV40-transformed cystic fibrosis bronchial epithelial cells (CFBE41o–), according to *PNAS, USA,* 85:5951 (1988), homozygous for the ΔF508 CFTR mutation were used. Cells were grown in Eagles minimal essential medium (MEM) supplemented with 10% fetal bovine serum (FBS), 2 mM L-Glutamine, 1% penicillin/streptomycin, at 37° C. in 5% $CO_2$-95% air. All the cultures were maintained in flasks or dishes pre-coated with an extracellular matrix of fibronectin-Vitrogen-bovine serum albumin (FN/V?BSA), according to In Vitro Cell Dev. Biol., 26:411 (1990). ElectroMax E. coli DH10B (Rec A1⁻) cells (Life technologies, CA) were used for the bacterial transformation studies.

EXAMPLE 2

Plasmid Construction

This example describes the procedure used for construction of plasmid.

The plasmid pZamp, was constructed by introducing the ampicillin gene from pcDNA3 (Invitrogen, Calif.) (fragment SalI-PvuII), into the multiple cloning site of pZeoSV (XhoI-PvuII) (Invitrogen, Calif.). The pZeoSV plasmid contains Zeocin™ antibiotic resistance ($zeo^r$) gene under CMV (eukaryotic) and EM-7 (prokaryotic) promoters. The resultant pZamp vector was then linearized at a unique, Xmal restriction enzyme cleavage site within the coding sequence of the $zeo^r$ gene.

The linearized vector was incubated with Klenow enzyme to fill in the overlapping bases and then ligated. The resultant vector, pZamp+4, seen in FIG. 1, carries a 4-bp insertion that eliminates the Xmal restriction site, and is no longer resistant to the Zeocin™ antibiotic in either prokaryotic or eukaryotic cells. The presence of the ampicillin gene allows for bacterial transformation and selection. Plasmid DNA was prepared by column chromatography (Qiagen, Calif.) in accordance with the manufacturer's instructions.

Other wild-type and mutated-version vector containing plasmid are prepared in the same way.

EXAMPLE 3

Fragment Preparation

This example describes the preparation of DNA fragments Zeo1 and Zeo3.

Two different DNA fragments, Zeo1 and Zeo3 (410- and 458-bp, respectively), as seen in FIG. 1, were employed for targeting. Both fragments contain the wt-$zeo^r$ gene sequence and were prepared by PCR as previously described in Hum. Mol. Genet., 7:1913 (1998).

Primers:

Z1Bss (5'GCGCGCGACGTCGCCGGAGCG-3') (sense) (SEQ ID NO: 1); and

Z2 (5'-AACAAGTTTCGAGGTCGACCCC-3') (antisense) (SEQ ID NO: 2).

Primers Z1Bss and Z2 were used to generate the Zeo1 fragment. Primers Z3 (5'-TAGGAGGGCCACCATGGCCA-3") (sense) (SEQ ID NO: 3) and Z2 (antisense) were used for the Zeo3 fragment.

The PCR conditions were as follows: initial denaturation, 95° C./2 minutes followed by 25 cycles of denaturation, 95° C./5 seconds; annealing 65° C./20 seconds; extension, 72° C./20 with a 7 minute extension in the final cycle. The PCR mixture contained: 0.2 mM dNTPs, 0.2 µM primers, 1× DMSO, 1× Pfu reaction buffer (10 mM Kcl, 10 mM ($NH_4$)$_2SO_4$ 20 mM Tris-HCl (pH 8.8), 2 mM $MgSO_4$, 0.1% Triton X-100, 100 ng/µl BSA) and 1U Pfu DNA polymerase (Stratagene, Calif.).

PCR products were subcloned into the pCR-Script vector (Stratagene, Calif.), sequenced and used as a template to generate preparative amounts of fragment for transfection.

Production of the targeting fragment involved amplification of 1–2 ng of linearized pCRZeo1 or pCRZeo3 plasmids in a 100 µl PCR mixture containing: 0.2 mM dNTPs, 0.2 µM primers, 1× DMSO, 10 mM Tris-HCl, 50 mM Kcl, 2 mM $MgCl_2$, 0.01% gelatin and 2.5 U AmpliTaq polymerase (Perkin Elmer, Calif.).

PCR products were purified from agarose gel, using the Qiaquick II kit (Qiagen, Calif.). The concentration of the PCR fragments used for targeting was determined using a Gibco-BRL DNA Mass Ladder. DNA fragments were rendered single-stranded by heat-denaturation at 95° C. for 10 minutes and, unless otherwise specified, cooled rapidly on ice before transfection.

DNA fragments for other genes are prepared in essentially the same way.

EXAMPLE 4

Co-Transfection Protocol

This example describes an experimental protocol used for co-transfection.

CFBE41o– cells were co-transfected with the mutant plasmid (pZamp+4) and DNA fragments under a variety of conditions. These conditions included using DNA fragments of different sizes (Zeo1 or Zeo3), using single- or double-stranded (ssDNA or dsDNA, respectively) and varying the ratios of fragment to mutant plasmid.

Successful correction of the mutant sequence was assessed from both transient and stable transfections. For the transient transfections, plasmid DNA was isolated from transfected cells and used to transform bacteria. Correction frequency was determined as the ratio of $zeo^r$ to total $amp^r$ colonies.

Control bacterial transformations included mixing extracts from epithelial cells transfected either with mutated plasmids or with DNA fragments alone. Assessment of stable transfections involved selection of epithelial cell clones containing corrected copies of the $zeo^r$ gene.

Clones from both transient and stable transfections were grown and genotypically analyzed by PCR amplification, restriction enzyme cleavage, DNA sequencing and/or Southern blot hybridization.

The same co-transfection protocol is used for co-transfection of cells with other plasmids.

EXAMPLE 5

Transfection Protocol

This example describes a protocol used for transfection of cells.

Cells were transfected with the cationic lipid DOTAP (Boehringer Mannheim), SuperFect (Starburst dendrimer, Qiagen) or electroporation using different molar ratios of pZamp+4 plasmid and targeting fragments. Cells were either grown on 6-well plates (DOTAP and SuperFect) or in T75 flasks (electroporation) until they reached 70–80% confluence.

Plasmid DNA-DOTAP complexes were formed in 100 µl of serum-free MEM at a negative to positive charge ratio of 1:4 (3 µg plasmid DNA:27.6 µg DOTAP). Complexes were allowed to form for 20 minutes, and then added to the cells in serum-free medium (1 ml final volume). After 4 hours, the medium was replaced with 2 ml of complete medium.

Cells were grown at 37° C. overnight and again transfected the following day with different amounts of the DNA fragment (heat denatured ssDNA or undenatured dsDNA) that was complexed with DOTAP at the same charge ration (1:4) used above.

The fragment DOTAP complex (100 µl) was then added to each well for an additional 4 hours in 1 ml of serum-free medium. After washing the cells with Hepes-buffered saline (HBS), 2 ml of complete medium were added to each well. The two transfections were performed on separate days to reduce cytotoxicity. A 6 hour period was sufficient for the cells to recover from transfection-induced stress and gave similar frequencies when compared to waiting 12 hours before the second transfection (data not shown).

Additional studies using plasmid/DOTAP/fragment complex yielded a correction frequency 10-fold lower than when the transfections were carried out in two steps. Plasmid DNA-SuperFect is obtained from QIAGEN, Ca., complexes were formed using a ratio of 3 µg plasmid DNA:6 µl of SuperFect. Different amounts of the DNA fragment-SuperFect complex was then added as described above. Transfections were carried out according to the manufacturer's instructions when using SuperFect or DOTAP.

Electroporation transfections were carried out as described previously in *Gene Ther.*, 3:859 (1996). Approximately $10^7$ cells were trypsinized, washed with cold PBS ($Mg^{2+}$ and $Ca^{2+}$ free) and then resuspended in 800 µl of the same PBS solution. From 6–18 µg of plasmid DNA (6 µg) was mixed with varying amounts of DNA fragment and added to the cell suspension. The total amount of DNA was kept constant (60 µg) in each set of experiments using carrier DNA, that is an unrelated DNA fragment.

The cell-DNA mixture was then incubated on ice for 10 minutes and electroporated at 4° C. using a BTX 300 Gene Pulser at a setting of 500µF., 240 mV and 200 msec in 0.4 cm transfection cuvettes. Cells were incubated on ice for an additional 10 min, diluted 1:20 in complete MEM and seeded into three T75 flasks.

EXAMPLE 6

Analysis of Transient Transfection

This example describes the analysis procedure used to detect transient transfection.

After transfection, cells were cultured at 37° C. for 48–72 hours and then harvested to isolate plasmid DNA. Cells were trypsinized and washed once with Hepes buffered saline (HBS). Episomal plasmid DNA was extracted using a modified alkaline lysis procedure according to *Mol. Cell Biol.*, 15:1759 (1995). When specified, plasmid DNA was also extracted from isolated nuclei according to *Pharm. Res.*, 7:1020 (1999).

Plasmid DNA was then incubated with RNaseA at 37° C. for 30 minutes and loaded onto a 0.7% SeaPlaque low-melting agarose gel. The relaxed and supercoiled forms of the plasmid as seen in FIG. 2, were extracted from the agarose gel with the QiaquickII kit (Qiagen, CA).

A 10 µl aliquot of each sample was used to transform *E. coli* DH10B cells by electroporation using a Bio-Rad Gene Pulser II (settings: 25 µF, 200 ohm and 1800 V; 0.1 cm cuvettes). After a 1 hour incubation at 37° C., aliquots of the transformed bacteria cells were plated onto low salt L-Broth (LB) (pH 7.5) plates supplemented with zeocin (25 µg/ml) and ampicillin (100 µg/ml) or with ampicillin alone. After an overnight incubation at 37° C., colonies were counted and targeting frequency determined. The frequency of correction was defined as the number of zeo$^r$ colonies divided by the total number of Amp$^r$ colonies in each experiment. The number of zeo$^r$ colonies were normalized to correct for variations in plating efficiency.

Individual bacterial clones were randomly picked and grown overnight in 5 ml LB plus antibiotics. Plasmid DNA was isolated with a Wizard miniprep purification system (Promega, WI.). A 200 ng plasmid sample from each clone was digested with XmaI at 25° C. and analyzed on a 0.8% agarose gel. In addition, 2 ng of each plasmid sample was used as template for a PCR analysis. The two primers used in the PCR analysis were outside the region of homology defined by the targeting fragment:

primer Z1 (5'-TACGACTCACTATAGGAGGGCC-3') (sense) (SEQ ID NO: 5) and primer Z4 (5'-CTACTCAAACCTGTTTGGTGTTG-3') (antisense) (SEQ ID NO: 6).

The PCR conditions were as follows: initial denaturation, 95° C./2 minutes followed by 25 cycles of denaturation, 95° C./5 seconds; annealing, 60° C./20 seconds; extension, 72° C./20 seconds with a 7 minute extension in the final cycle.

All PCR amplifications were carried out in a Perkin Elmer Thermal Cycler (9600). The PCR amplification products (574-bp), were digested with XmaI and analyzed on a 1.8% agarose gel. In addition, an aliquot of the isolated plasmid DNA was sequenced with an ABI 373A sequencer in both directions, using primers Z1 and Z4.

EXAMPLE 7

Analysis of Stable Transfection

This example describes the procedure used for analysis of stable transfection.

After transfection (48 hours), the CFBE410- cells were plated into 10 cm dishes and exposed to Zeocin™ containing medium every 2 days. Cells were grown until they formed colonies (~100 cells/colony) and isolated using cloning cylinders. Individual clones of zeo$^r$ epithelial cells were subcultured into T75 flasks and grown under continuous selection to 90% confluence.

Genomic DNA was isolated from each epithelial cell clone and analyzed by PCR and/or Southern blot hybridization. PCR analysis entailed amplification of 200 ng of genomic DNA with Z1 and Z4 primers under the conditions described above. The amplification product was digested with XmaI at 25° C. and analyzed on a 1.8% agarose gel. Southern blot hybridization analysis involved digesting 10 µg of DNA from individual clones with EcoRI and subsequent electrophoresis on a 0.8% agarose gels in TAE buffer (0.04 M Tris-Acetate, 1 mM EDTA).

The DNA was transferred from the gel to a nylon membrane (Hybond-N) by capillary action and crosslinked to the membrane using the UV Stratalinker 1800 (Stratagen, Calif.). Hybridization was performed as previously described at 65° C. for 16 hours with two different radioactively randomly labeled probes.

The first probe was a 613-bp CMV-specific probe generated by PCR amplification using the same conditions mentioned above with primers CM3: 5'CATAACTTACGGTAAATGGCCCG-3' (sense) (SEQ ID NO: 7); and CMV4: 5'CGTTCCAATGCACCGTTCCCG-3$^1$ (antisense) (SEQ ID NO: 8).

The first probe was removed by washing the membrane at 100° C. in 0.1% SDS for 5 minutes. The second probe, the 410-bp Zeo1 fragment, was specific for zeo$^r$ sequences.

What is claimed:

1. A method for determimng efficiency of sequence-specific modification of intracellular DNA by homologous replacement in the nucleus of eukaryotic cells, the method comprising:
 (a) co-transfecting eukaryotic cells with:
  (i) an expression vector comprising a mutant marker gene and a second marker gene; and
  (ii) a gene targeting element consisting of sufficient wild type gene sequence to correct by homologous replacement the mutant marker gene set forth in (i) and lacking expression control sequence;
 (b) isolating a nuclear fraction from the transfected cells;
 (c) assaying the nuclear fraction for the presence of wild type marker gene and the second marker gene, wherein the assaying comprises:

(i) extracting the vector from the nuclear fraction;
(ii) transforming bacteria with the extracted vector; and
(iii) growing the transformed bacteria under conditions sufficient to reveal presence of the wild type marker gene and the second marker gene; and (d) determining; the proportion of corrected sequences, whereby the number of bacteria in which the wild type marker gene is present is divided by the number of bacteria in which the second marker gene is present; the proportion present in the nuclear fraction being indicative of efficiency of sequence-specific modification of intracellular DNA by homologous replacement in the nucleus, whereby a higher proportion indicates more efficient replacement.

2. The method of claim 1, wherein mutation to create the mutant marker is introduced into the mutant marker gene by site-directed mutagenesis or cassette insertion.

3. The method of claim 1, wherein the mutant marker gene is produced by incubating a vector comprising a wild-type marker gene with an oligonucleotide containing a desired mutation under conditions sufficient to permit annealing of the oligonucleotide and the vector, and to permit extension of the oligonucleotide to produce a mutant marker gene.

4. The method of claim 1, wherein the mutant marker gene is a selectable or reporter gene.

5. The method of claim 4, wherein the selectable gene is selected from the group consisting of aminoglycoside phosphotransferase II gene (neo G418, APH), hygromycin-B-phosphotransferase gene (hygr), bleomycin resistance gene (bleo),zeotin resistance gene (zeo), sulfonamide resistance gene (sull), hypoxantine phosphoribosyl transferase gene (HPRT), adentine phosphoribosyl transferase gene (APRT), adenosine deaminase gene (ADA), cytosine deaminase gene (CDA), dihydrofolate reductase gene (DHFR), histidinol dehydrogenase gene (hisD), puromycin-N-acetyl transferase gene (PAC), thymidine kinase gene (TK), xanthine-guanine phosphoribosyltransferase gene (gpt), diphtheria toxin gene (DT) and herpes simplex virus thymidine kinase gene (HSV-TK).

6. The method of claim 4, wherein the selectable gene is a zeocin resistance gene.

7. The method of claim 4, wherein the reporter gene is selected from the group consisting of chloramphenicol aceryl transferase gene (CAT), β-galactosidase gene (β-gal), luciferase gene (luc), alkaline phosphatase gene (AP), secreted alkaline phosphatase gene (SEAP), β-glucuronidase gene (GUS), green fluorescent protein gene (GFP), human growth hormone gene (bGH) and β-lactamase gene (β-lac).

8. The method of claim 1, wherein the transfecting of step (a) comprises electroporation, microinjection, cationic lipid delivery, anionic lipid delivery, cationic polymer delivery or cationic polyamino acid delivery.

9. The method of claim 1, further comprising purifying the extracted vector prior to the transforming of step (c)(ii).

10. The method of claim 1, wherein the mutant marker gene is a zeocin resistance gene and the conditions of step (iii) comprise growing the transformed bacteria in the presence of zeocin.

11. The method of claim 1, wherein the mutant marker gene comprises a zeocin resistance gene and the second marker gene comprises an ampicillin resistance gene.

12. The method of claim 11, wherein the conditions sufficient to reveal presence of the wild type marker gene comprise:
growing the transformed bacteria in the presence of ampicillin and in the presence of zeocin;
and wherein the determining of step (d) comprises dividing the number of bacterial colonies grown in the presence of zeocin by the number of bacterial colonies grown in the presence of ampicillin to determine the efficiency of sequence-specific modication of intracellular DNA by homologous replacement in the nucleus.

13. The method of claim 1, wherein the assaying of step (c) comprises PCR amplification of wild type marker gene, restriction digestion, DNA sequencing or Southern hybridization.

14. The method of claim 1, wherein the mutant marker gene comprises pZamp+4 as shown in FIG. 1.

15. The method of claim 1, wherein the gene targeting element consists of a 410 bp fragment, Zeo1.

16. The method of claim 15, wherein the gene targeting element is prepared by PCR using primers having the nucleotide sequences shown in SEQ ID NO: 1 and SEQ ID NO: 2.

17. The method of claim 1, wherein the gene targeting element consists of a 458 bp fragment, Zeo3.

18. The method of claim 17, wherein the gene targeting element is prepared by PCR using primers having the nucleotide sequences shown in SEQ ID NO: 3 and SEQ ID NO: 2.

19. The method of claim 1, further comprising isolating a whole cell lysate from the transfected cells, assaying the whole cell lysate as in step (c), and comparing the number of bacteria transformed with vector extracted from the whole cell lysate in which the second marker gene is present to the number of bacteria transformed with the nuclear fraction in which the second marker gene is present.

* * * * *